United States Patent [19]

Goto et al.

[11] Patent Number: 5,434,179

[45] Date of Patent: Jul. 18, 1995

[54] METHOD FOR IMPROVING BRAIN FUNCTION USING CHOLINESTERASE-INHIBITING AMINOKETONE COMPOUNDS

[75] Inventors: Giichi Goto, Toyono; Akinobu Nagaoka, Kawanishi; Yuji Ishihara, Itami, all of Japan

[73] Assignee: Takeda Chemical Industries, Ltd., Osaka, Japan

[21] Appl. No.: 215,619

[22] Filed: Mar. 22, 1994

Related U.S. Application Data

[62] Division of Ser. No. 905, Jan. 6, 1993, abandoned.

[30] Foreign Application Priority Data

Jun. 6, 1989 [JP] Japan ................... 1-143342

[51] Int. Cl.⁶ ................... A61K 31/40; A61K 31/135
[52] U.S. Cl. ................... 514/429; 514/655
[58] Field of Search ................... 514/429, 655

[56] References Cited

U.S. PATENT DOCUMENTS 3,197,507 7/1965 Freed et al. .................. 564/345
4,073,797 2/1978 Ramuz .

FOREIGN PATENT DOCUMENTS 214094  3/1987  European Pat. Off. .
1334884 10/1973  United Kingdom .
1489086 10/1977  United Kingdom .
1489087 10/1977  United Kingdom .
1489088 10/1977  United Kingdom .

OTHER PUBLICATIONS

*Chemical Abstracts*, vol. 72, No. 1, p. 302, item 3333h (1970).
*Journal of Medical Chemistry*, vol. 32, 1988, pp. 105–108, "Synthesis and Antiallergy Activity of 4-(-Diarylhydroxymethyl)-1-[3-(aryloxy)propyl]piperidines and Structurally Related Compounds".
*Chemical Abstracts*, vol., 64, 1966, p. 8091, Abstract of U.S. Pat. No. 3,197,507.

*Primary Examiner*—Robert W. Ramsuer
*Assistant Examiner*—Michael G. Ambrose
*Attorney, Agent, or Firm*—Foley & Lardner

[57] ABSTRACT

An aminoketone compound of the formula

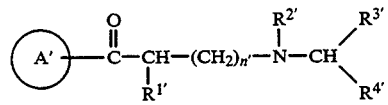

wherein ring A' means a five through eight-membered cyclic group which may be substituted and may contain one or two hetero atom(s) of O, S, N, as the ring-constituents; $R^{1'}$ means a hydrogen atom or a hydrocarbon residue which may be substituted; $R^{2'}$ means a hydrogen atom or a lower alkyl group; $R^{3'}$ means an aromatic group which may be substituted; $R^{4'}$ means a hydrogen atom, a lower alkyl group or aromatic group which may be substituted; $n'$ means an integer of 2 to 7, or a salt thereof, is useful as an cholinesterase inhibitors and a cerebral function ameliorating agent.

21 Claims, No Drawings

METHOD FOR IMPROVING BRAIN FUNCTION USING CHOLINESTERASE-INHIBITING AMINOKETONE COMPOUNDS

This application is a division of Ser. No. 08/000,905 filed Jan. 6, 1993, abandoned.

BACKGROUND OF THE INVENTION

1. Field of the Invention

The present invention relates to aminoketone derivatives and their salts, which are of value as medicinals and particularly as brain function ameliorating agents which may be indicated in conditions such as senile dementia and Alzheimer's disease.

With the proportion of elderly people in the total population being on a steady increase, a number of compounds claimed to have brain function ameliorating activity have been introduced. Among such compounds, the cholinesterase inhibitor physostigmine has been found to possess a brain function ameliorating action.

Physostigmine, however, has several drawbacks, among which are a short duration of action and a high toxicity potential.

The object of the present invention is to provide a cholinesterase inhibitor composition which is more potent, longer-acting and less toxic than any compound hitherto known to have brain function improving activity.

In (1) Journal of Medicinal Chemistry 32, 105 (1989) (as a by-product of reaction), (2) Japanese Patent Application KOKAI No. 95267/1975 (as an intermediate compound for synthesis), (3) Japanese Patent Application KOKAI No. 20134/1972 (as central nervous system depressant etc.) and (4) U.S. Pat. No. 3,197,507 (as central nervous system depressant etc.), there are disclosed the following compounds (1)–(4), respectively, but there is no mention of cholinesterase inhibiting activity and a brain function ameliorating agent.

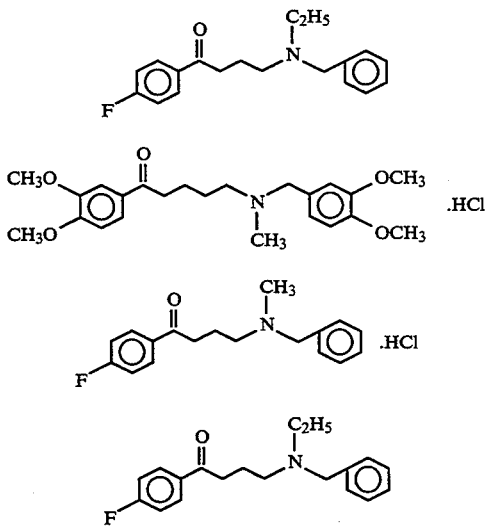

The inventors of the present invention explored a class of compounds which could be of value as brain function improving agents having anticholinesterase activity and found that an aminoketone derivative which has the formula (I′)

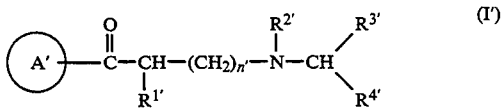

wherein ring A′ designates a five through eight-membered cyclic group which may be substituted and may contain one or two hetero atom(s) of O, S, N, as the ring-constituents; $R^{1'}$ means a hydrogen atom or a hydrocarbon residue which may be substituted; $R^{2'}$ means a hydrogen atom or a lower alkyl group; $R^{3'}$ means an aromatic group which may be substituted; $R^{4'}$ means a hydrogen atom, a lower alkyl group or an aromatic group which may be substituted; $n'$ means an integer of 2 to 7, or a physiologically acceptable salt thereof has excellent brain function ameliorating activity. The inventors further succeeded in the creation of novel compounds, which have not been described in any literatures, among the compounds of the formula (I′), and accomplished the present invention.

SUMMARY OF THE INVENTION

The present invention is, therefore, directed to a cholinesterase inhibitor composition containing a compound of the above formula (I′) [hereinafter referred to sometimes as compound (I′)] or a salt thereof, and an aminoketone derivative [hereinafter referred to sometimes as compound (I)] of the following formula (I)

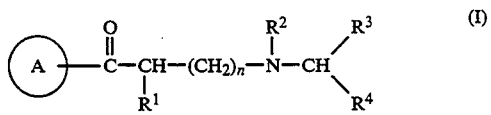

wherein ring A represents a five through eight-membered cyclic group which may be substituted and may contain one or two hetero atom(s) of O, S, N as the ring-constituents; $R^1$ means a hydrogen atom or a hydrocarbon residue which may be substituted; $R^2$ means a hydrogen atom or a lower alkyl group; $R^3$ means an aromatic group which may be substituted; $R^4$ means a hydrogen atom, a lower alkyl group or an aromatic group which may be substituted; n means an integer of 2 to 7 or a physiologically acceptable salt thereof, provided that when the ring A is a benzene ring having p-fluorine atom to the position of the carbonyl group, n is an integer of 3 to 7 and or provided that when the ring A is a benzene ring having p- and m-methoxy groups to the position of the carbonyl group, $R^2$ is a lower alkyl group having 2 or more carbon atoms and a process for production thereof.

DESCRIPTION OF THE PREFERRED EMBODIMENT

Referring to the above formula (I) and (I′), the "hydrocarbon residue" in the definition "hydrocarbon residue, which may optionally be substituted" given for $R^1$ and $R^{1'}$ includes, among others, hydrocarbon residues which are acyclic or cyclic, saturated or unsaturated as well as residues resulting from various combinations of such hydrocarbon residues. As acyclic saturated hydrocarbon residues, there may be mentioned, for example, straight or branched $C_{1-11}$ alkyl groups (e.g. methyl, ethyl, n-propyl, i-propyl, n-butyl, i-butyl, tert-butyl, n-pentyl, n-hexyl).

As acyclic unsaturated hydrocarbon residues, there may be mentioned straight or branched $C_{2-4}$ alkenyl groups (e.g. vinyl, allyl, 2-butenyl) and straight or branched $C_{2-4}$ alkynyl groups (e.g. propargyl, 2-butynyl).

As cyclic saturated hydrocarbon residues, there may be mentioned monocyclic $C_{3-7}$ cycloalkyl groups (e.g. cyclobutyl, cyclopentyl, cyclohexyl) and bridged saturated $C_{8-14}$ hydrocarbon residues [e.g. bicyclo[3.2.1]-oct-2-yl, bicyclo[3.3.1]nonan-2-yl, adamantan-1-yl]. As cyclic unsaturated hydrocarbon residues, there may be mentioned phenyl, naphthyl and the like.

As lower alkyls represented by $R^2$, $R^4$, $R^{2'}$ and $R^{4'}$, there may be mentioned $C_{1-6}$ alkyl (e.g. methyl, ethyl, n-propyl, i-propyl, n-butyl, i-butyl, tert-butyl, n-pentyl, n-hexyl).

As substituents which the acyclic saturated, acyclic unsaturated and cyclic saturated hydrocarbon residues may optionally have, there may be mentioned halogen atoms (e.g. fluorine, chlorine, bromine, iodine), nitro, cyano, hydroxy, $C_{1-4}$ alkoxy (e.g. methoxy, ethoxy, propoxy, butyloxy, isopropoxy, etc.), $C_{1-4}$ alkylthio (e.g. methylthio, ethylthio, propylthio, etc.), amino, mono- or di-$C_{1-4}$ alkyl-substituted amino (e.g. methylamino, ethylamino, propylamino, dimethylamino, diethylamino, etc.), $C_{1-4}$ alkylcarbonylamino (e.g. acetylamino, propionylamino, butyrylamino, etc.), $C_{1-4}$ alkylsulfonylamino (e.g. methylsulfonylamino, ethylsulfonylamino, etc.), $C_{1-4}$ alkoxycarbonyl (e.g. methoxycarbonyl, ethoxycarbonyl, propoxycarbonyl, etc.), hydroxycarbonyl, $C_{1-6}$ alkylcarbonyl (e.g. methylcarbonyl, ethylcarbonyl, propylcarbonyl, etc.), carbamoyl, mono- or di-$C_{1-4}$ alkyl-substituted carbamoyl (e.g. methylcarbamoyl, ethylcarbamoyl, dimethylcarbamoyl, diethylcarbamoyl, etc.), $C_{1-6}$ alkylsulfonyl (e.g. methylsulfonyl, ethylsulfonyl, propylsulfonyl, etc.).

Referring to the above formula (I) and (I'), "the aromatic group" of the "aromatic group which may be substituted", denoted by $R^3$, $R^4$ and $R^{3'}$, $R^{4'}$, there may be mentioned phenyl or naphthyl.

The substituents groups which may substitute the aromatic groups of $R^3$, $R^4$, $R^{3'}$ and $R^{4'}$ and the cyclic unsaturated hydrocarbon residues of $R^1$ and $R^{1'}$ include $C_{1-4}$ alkyl (e.g. methyl, ethyl, propyl, butyl, etc.), halogen atoms (e.g. fluorine, chlorine, bromine, iodine), nitro, cyano, hydroxy, $C_{1-4}$ alkoxy (e.g. methoxy, ethoxy, propyloxy, butyloxy, isopropyloxy), $C_{1-4}$ alkylthio (e.g. methylthio, ethylthio, propylthio, isopropylthio, butylthio), amino, mono- or di-$C_{1-4}$ alkyl-substituted amino (e.g. methylamino, ethylamino, propylamino, dimethylamino, diethylamino), $C_{1-4}$ alkylcarbonylamino (e.g. acetylamino, propionylamino, butyrylamino, etc.), aminocarbonyloxy, mono- or di-$C_{1-4}$ alkyl-substituted aminocarbonyloxy (e.g. methylaminocarbonyloxy, ethylaminocarbonyloxy, dimethylaminocarbonyloxy, diethylaminocarbonyloxy, etc.), $C_{1-4}$ alkylsulfonylamino (e.g. methylsulfonylamino, ethylsulfonylamino, propylsulfonylamino, etc.), $C_{1-4}$ alkoxycarbonyl (e.g. methoxycarbonyl, ethoxycarbonyl, propoxycarbonyl, isobutoxycarbonyl), hydroxycarbonyl, $C_{1-6}$ alkylcarbonyl (e.g. methylcarbonyl, ethylcarbonyl, butylcarbonyl, cyclohexylcarbonyl), carbamoyl, mono- or di-$C_{1-4}$ alkyl-substituted carbamoyl (e.g. methylcarbamoyl, ethylcarbamoyl, propylcarbamoyl, butylcarbamoyl, diethylcarbamoyl, dibutylcarbamoyl, etc.), $C_{1-6}$ alkylsulfonyl (e.g. methylsulfonyl, ethylsulfonyl, propylsulfonyl, cyclopentylsulfonyl, cyclohexylsulfonyl, etc.), as well as phenyl, naphtyl, phenoxy, benzoyl, phenoxycarbonyl, phenyl $C_{1-4}$ alkylcarbamoyl, phenylcarbamoyl, phenyl $C_{1-4}$ alkylcarbonylamino, benzoylamino, phenyl $C_{1-4}$ alkylsulfonyl, phenylsulfonyl, phenyl $C_{1-4}$ alkylsulphynyl, phenyl $C_{1-4}$ alkylsulfonylamino and phenylsulfonylamino, each of which may have 1 to 4 substituents. Here, the substituents on this phenyl or naphtyl include, among others, $C_{1-4}$ alkyl (e.g. methyl, ethyl, propyl, butyl, isopropyl, etc.), $C_{1-4}$ alkoxy (e.g. methoxy, ethoxy, n-propyloxy, i-propyloxy, n-butyloxy, etc.), halogen atoms (e.g. chlorine, bromine, iodine, etc.), hydroxy, benzyloxy, amino, mono- or di-$C_{1-4}$ alkyl-substituted amino, nitro and $C_{1-4}$ alkoxycarbonyl.

The preferred number of substituent groups substituting the aromatic group is 1 to 3.

Referring to the above formulas (I) and (I'), the ring A and A' may be a carbocycle or a heterocycle containing 1 to 2 hetero atoms selected from among O, S and N, and may be saturated or unsaturated. As ring A and A', mention may be made of, for example, benzene naphtalene, pyridine, furan thiophene and quinoline each of which may be substituted.

The substituted groups which may substitute ring A and A' include, among others, $C_{1-4}$ alkyl (e.g. methyl, ethyl, propyl, butyl, etc.), halogen atoms (e.g. fluorine, chlorine, bromine, iodine, etc.), nitro, cyano, hydroxy, $C_{1-4}$ alkoxy (e.g. methoxy, ethoxy, propyloxy, butyloxy, isopropyloxy, etc.), $C_{1-4}$ alkylthio (e.g. methylthio, ethylthio, propylthio, isopropylthio, butylthio, etc.), amino, mono- or di-$C_{1-4}$ alkyl-substituted amino (e.g. methylamino, ethylamino, propylamino, dimethylamino, diethylamino, etc.), 5 to 8-membered cyclic amino (e.g. pyrrolidino, piperidino, hexamethyleneimino, etc.), $C_{1-4}$ alkyl-carbonylamino (e.g. acetylamino, propionylamino, butyrylamino, etc.), $C_{1-4}$ alkylsulfonylamino (e.g. methylsulfonylamino, ethylsulfonylamino, propylsulfonylamino, etc.), $C_{1-4}$ alkoxycarbonyl (e.g. methoxycarbonyl, ethoxycarbonyl, propoxycarbonyl, isobuthoxycarbonyl, etc.), hydroxycarbonyl, $C_{1-6}$ alkylcarbonyl (e.g. methylcarbonyl, ethylcarbonyl, butylcarbonyl, cyclohexylcarbonyl, etc.), carbamoyl, mono- or di-$C_{1-4}$ alkyl-substituted carbamoyl (e.g. methylcarbamoyl, ethylcarbamoyl, propylcarbamoyl, butylcarbamoyl, diethylcarbamoyl, dibutylcarbamoyl, etc.), $C_{1-8}$ alkylsulfonyl (e.g. methylsulfonyl, ethylsulfonyl, propylsulfonyl, cyclopentylsulfonyl, cyclohexylsulfonyl, etc.), as well as phenyl, naphtyl, phenoxy, benzoyl, phenoxycarbonyl, phenyl $C_{1-4}$ alkylcarbamoyl, phenylcarbamoyl, phenyl $C_{1-4}$ alkylcarbonylamino, benzoylamino, phenyl $C_{1-4}$ alkylsulfonyl, phenylsulfonyl, phenyl $C_{1-4}$ alkylsulfinyl, phenyl $C_{1-4}$ alkylsulfonylamino and phenylsulfonylamino, each of which may have 1 to 4 substituents. Here, the substituents on the phenyl or naphtyl ring include, among others, $C_{1-4}$ alkyl (e.g. methyl, ethyl, propyl, butyl, isopropyl, etc.), $C_{1-4}$ alkoxy (e.g. methoxy, ethoxy, n-propyloxy, i-propyloxy, n-butyloxy, etc.), halogen atoms (e.g. chlorine, bromine, iodine, etc.), hydroxy, benzyloxy, amino, mono- or di-$C_{1-4}$ alkyl-substituted amino (e.g. methylamino, dimethylamino, etc.), nitro, $C_{1-4}$ alkoxycarbonyl. Preferably, the ring A and A' have 1 to 3 substituents (which may be the same or different) selected from the above-mentioned various substituents.

Preferred species of the compound of the formula (I) or (I') include the following.

$R^1$ and $R^{1'}$ preferably mean hydrogen atom. $R^2$ and $R^{2'}$ preferably mean methyl, ethyl or i-propyl, etc., and more desirably, mean ethyl.

$R^3$ and $R^{3'}$ preferably mean an unsubstituted phenyl or a substituted phenyl which has 1 to 2 of alkoxy such as methoxy and ethoxy, and more desirably means phenyl, 2-methoxyphenyl and 3-methoxyphenyl.

$R^4$ and $R^{4'}$ preferably mean a hydrogen atom.

The symbols n and n' preferably stand for 3, 4 or 5.

The ring A and A' preferably designate a benzene ring which may be substituted.

As the substituents for the ring A and A', among those mentioned hereinbefore, there may be preferably mentioned $C_{1-4}$ alkoxy, nitro, cyano, halogen atoms, amino, $C_{1-4}$ alkylcarbonylamino, $C_{1-4}$ alkyl-sulfonyl, 5- to 8-membered cycloamino, mono- or di-$C_{1-4}$ alkyl-amino group and so on. There may be mentioned more preferably $C_{1-4}$ alkoxy, halogen atoms and 5- to 8-membered cycloaminos.

The compounds (I) and (I') of the present invention may be provided in the form of an acid addition salt, particularly a physiologically acceptable acid-addition salt.

Examples of such salts include salts with an inorganic acid (e.g. hydrochloric acid, nitric acid, phosphoric acid, hydrobromic acid, sulfuric acid, etc.), or with an organic acid (acetic acid, formic acid, propionic acid, fumaric acid, maleic acid, succinic acid, tartaric acid, citric acid, malic acid, oxalic acid, benzoic acid, methanesulfonic acid, benzenesulfonic acid, etc.).

When the objective compounds (I) and (I') have an acid group such as —COOH, they may be provided in the form of a salt with an inorganic base (e.g. sodium, potassium, calcium, magnesium, ammonia, etc.) or an organic base such as triethylamine.

The process for production of novel compound (I) according to this invention is described below.

It should be understood that the term "compound (I) as used in the following description means not only the compound (I) as such but also its salt.

Compound (I) can be produced by reacting, for example, a compound of the formula (I)

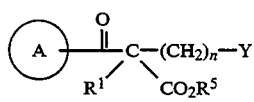
(II)

wherein Y means a leaving group, such as halogen, alkyl or arylsulfonyloxy, etc., $R^5$ means a lower alkyl group and all other symbols are respectively as defined hereinbefore with a compound of the formula (III)

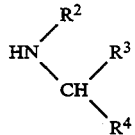
(III)

wherein all symbols are as defined hereinbefore or a salt thereof, and subject the thus obtained compound to hydrolysis and decarboxylation according to any of the known processes, for example the process described in Journal of Organic Chemistry 33, 2457 (1968), or any process analogous thereto.

As lower alkyl represented by $R^5$, there may be mentioned $C_{1-6}$ alkyl (e.g. methyl, ethyl, n-propyl, i-propyl, n-butyl, i-butyl, tert-butyl, n-pentyl, n-hexyl, etc.).

The alkyl moiety of said alkyl- or arylsulfonyloxy group Y includes, among others, $C_{1-4}$ alkyl groups such as methyl, ethyl, propyl, etc. and the aryl moiety of Y includes, among others, phenyl and substituted phenyl such as p-methylphenyl and so on. The salt of compound (III) includes various acid addition salts such as those mentioned for the salt of compound (I). The reaction of the compound (II) with the compound (III) is carried out using a solvent or in the absence of a solvent. The reaction can also be carried out in the presence of a base or without using a base.

The base mentioned just above can be selected from among inorganic bases such as sodium carbonate, potassium carbonate, lithium carbonate, sodium hydroxide, potassium hydroxide, sodium methoxide, sodium ethoxide, sodium hydride, etc. and organic bases such as pyridine, 4-dimethylaminopyridine, triethylamine and so on. The solvent, if used, can be selected from among various solvents which do not interfere with the reaction, e.g. lower alcohols such as methanol, ethanol, propanol, isopropyl alcohol, n-butanol, t-butanol, etc., aromatic hydrocarbons such as toluene, benzene, xylene, etc., various amides such as dimethylformamide, dimethylacetamide, hexamethylphosphonotriamide, etc., and various esters such as ethyl acetate, butyl acetate, and so on. This reaction can be conducted under cooling (about 0° to 10° C.), at room temperature (about 10° to 40° C.) or under heating (about 40° to 120° C.) and the reaction time is generally 10 minutes to 48 hours and preferably about 2 to 16 hours. The preferred proportion of compound (III) is generally 3 to 5.0 moles to each mole of compound (II). The amount of the base, if used, is generally at least equimolar and preferably 1.1 to 5 equivalents based on compound (III). If desired, this reaction can be conducted in the presence of an iodide such as sodium iodide, potassium iodide, lithium iodide or the like. The amount of such iodide, if used, is generally 1 to 5 equivalents and preferably 1.1 to 1.5 equivalents relative to compound (II).

The above compound of the formula (II) can be prepared by any of the known processes, for example the processes described in Journal of Organic Chemistry 33, 2457 (1968) and 39, 2637 (1974), or any process analogous thereto.

Compound (I) can be also produced by, for example reacting a compound of the formula (IV)

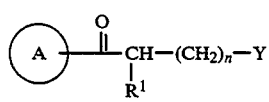
(IV)

wherein all symbols are respectively as defined hereinbefore, with a compound of the formula (III) or a salt thereof, under analogous condition to that of the reaction of compound (II) with compound (III).

The compound of the above formula (IV) can be produced by any of the known processes, for example the processes described in Journal of Organic Chemistry 33, 2457 (1968) and 39, 2637 (1974) or any analogous processes thereto.

Further, the compound of the formula (I), wherein ring A is substituted with amino, a 5- to 8-membered cycloamino group and/or a mono- or di-$C_{1-4}$ alkylamino group, can be also produced by reacting a compound of the formula (V)

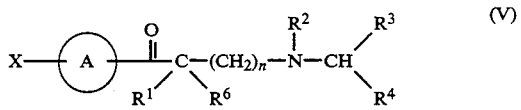

wherein X means a halogen atom, $R^6$ means a hydrogen atom or $-CO_2R^5$ and all other symbols are respectively as defined hereinbefore, with the corresponding amine.

The compound (I) can be produced by other known processes or processes analogous thereto as well.

The compounds (I) or (I') of the present invention act on the central nervous system of mammals, where they exert potent anticholinesterase activity to show an excellent anti-amnesic action against various types of induced amnesia in man and animals (e.g. mice).

Compared with physostigmine, the compound (I) or (I') of the invention is characterized by a distinct separation of its action on central nerves from that on peripheral nerves, scarcely producing peripheral nervous symptoms such as spasm, salivation and diarrhea, if any, at antiamnesically effective doses and being long-acting and low in toxicity. Moreover, the compound produces remarkable effects on oral administration.

Therefore, the compound (I) or (I') is useful as a brain function ameliorating agent for mammals including man.

The diseases in which the compound (I) or (I') may be indicated are, for example senile dementia, Alzheimer's disease, Huntington's chorea, hyperkinesia and mania. The compound can be used in the prevention or treatment of these diseases.

The compound of the present invention can be administered, orally or parenterally, to mammalian animals inclusive of man in various dosage forms such as tablets, granules, capsules, injections, suppositories and so on. While the dosage depends on such factors as the type and symptoms of the disease to be treated, the daily oral dosage per adult human is about 0.001 to 100 mg, preferably about 0.01 to 30 mg, and more desirably about 0.3 to 10 mg.

The compound according to the present invention acts on the central nervous system of mammals and exerts potent anticholinesterase activity. Therefore, it can be used in the prevention and treatment of various diseases such as senile dementia, Alzheimer's disease, Huntington's chorea and so on. Thus, the compound is a useful drug.

The following working, reference, preparation and test examples are intended to illustrate the invention in further detail and should by no means be construed as defining the scope of the invention.

In the working and reference examples which appear hereinafter, elution procedures in column chromatography were carried out under monitoring by thin-layer chromatography (TLC) unless otherwise indicated. In TLC monitoring, Merck's 60 $F_{254}$ was used as the TLC plate, the eluent for column chromatography as the developing solvent, and an UV detector as the spot detection means. For identification of the fractions rich in each objective compound, the detection method comprising spraying the TLC plate with a 48% HBr solution, hydrolyzing it by heating, spraying a ninhydrin reagent and reheating to detect a change of color to red-reddish purple was used in conjunction. Furthermore, unless otherwise indicated, Merck's silicagel 60 (70~230 mesh) was used as silica gel for column chromatography.

It should also be understood that the terms "atmospheric temperature" and "room temperature" are both used to mean a temperature within the range of about 5° C. to 40° C. and the terms "atmospheric pressure" are used to mean a pressure in the neighborhood of one atmosphere.

All percents (%) are by weight unless otherwise indicated.

REFERENCE EXAMPLE 1

Ethyl bromo-1-(3,4-dimethoxyphenyl)-1-oxoheptane-2-carboxylate

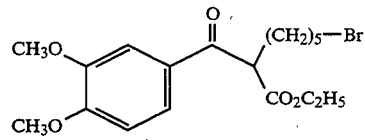

To a solution of ethyl 3-oxo-3-(3,4-dimethoxyphenyl)propionate (1.1 g) in dimethylformamide (10 ml) was added sodium hydride (0.13 g) and the mixture was stirred at room temperature for 30 minutes. Then, 1,5-dibromopentane (2.1 g) was added and the mixture was further stirred for 2 hours. The reaction was then stopped by adding water and the product was extracted into dichloromethane.

The extract was washed with water and dried over anhydrous sodium sulfate and the solvent was distilled off under reduced pressure. The oily residue was subjected to sillica gel column chromatography (eluent: dichloromethane-ethyl acetate=20:1 (V/V)) and the fractions containing the desired compound were pooled and then the solvent was distilled off to give 1.5 g of colorless oily substance.

Elemental analysis, $C_{18}H_{25}BrO_5$ Calcd.: C 53.87 H 6.28 Found : C 53.92 H 6.25

REFERENCE EXAMPLE 2

According to the same manner as Reference Example 1, the compounds shown in Table 1 were obtained.

TABLE 1

B—(CH$_2$)$_n$—Br

| Compound No. | B | n | Molecular formula | Elemental analysis Calcd. (Found) | | |
|---|---|---|---|---|---|---|
| | | | | C | H | N |
| 1 | CH$_3$O—[benzene ring with CH$_3$O]—C(=O)—CH(CO$_2$C$_2$H$_5$)— | 4 | $C_{17}H_{23}BrO_5$ (Oily) | 52.72 (52.64) | 5.99 (5.90) | |

TABLE 1-continued

B—(CH$_2$)$_n$—Br

| Compound No. | B | n | Molecular formula | Elemental analysis Calcd. (Found) | | |
|---|---|---|---|---|---|---|
| | | | | C | H | N |
| 2 | 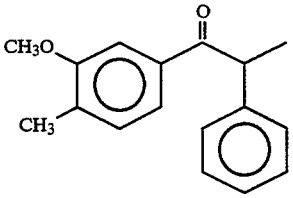 | 5 | C$_{21}$H$_{25}$BrO$_3$ (Oily) | 62.23 (62.09 | 6.22 6.15) | |
| 3 | 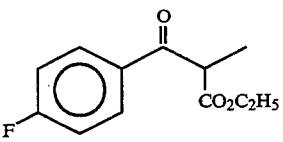 | 4 | C$_{15}$H$_{18}$BrFO$_3$ (Oily) | 52.19 (52.01 | 5.26 5.24) | |
| 4 | 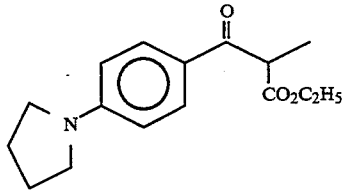 | 4 | C$_{19}$H$_{26}$NBrO$_3$ | 57.58 (57.51 | 6.61 6.45 | 3.53 3.48) |

EXAMPLE 1

N-[7-(3,4-dimethoxyphenyl)-7-oxoheptyl]-N-ethyl-N-(2-methoxyphenyl)methyl]amine hydrochloride

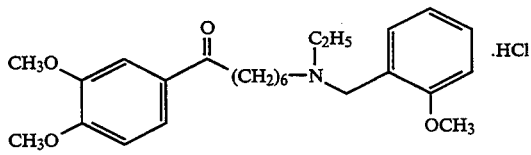

A solution of the ethyl 7-bromo-1-(3,4-dimethoxyphenyl)-1-oxoheptane-2-carboxylate prepared by Reference Example 1 (0.35 g) and N-ethyl-N-[(2methoxyphenyl)methyl]amine (0.29 g) in toluene (8 ml) was refluxed for 12 hours and then the solvent was distilled off under reduced pressure. The remaining oily substance was dissolved in ethanol (3 ml) and after addition of a solution of potassium hydroxide (0.3 g) in water (0.5 ml), the mixture was refluxed for 6 hours. The solvent was distilled off under reduced pressure, and then water (10 ml) was added to the residue. The product was extracted into dichloromethane, and the extract was washed with water and then dried over anhydrous sodium sulfate. The solvent was distilled off under reduced pressure. The remaining oily substance was subjected to column chromatography (eluent:ethylacetate—methanol=20:1 (V/V)). The fractions containing the desired compound were pooled and then solvent was distilled off under reduced pressure. To the residue was added a 3-N hydrogen chloride-ethanol solution (0.56 ml) and the solvent was distilled off to give a hygroscopic amorphous powder (0.3 g).

Elemental analysis C$_{25}$H$_{35}$NO$_4$.HCl Calcd.: C 66.73 H 8.06 N 3.11 Found: C 66.52 H 7.99 N 3.05

EXAMPLE 2

N-[6-(3,4-dimethoxyphenyl)-6-oxohexyl]-N-ethyl-N-[(2-methoxyphenyl)methyl]amine fumarate

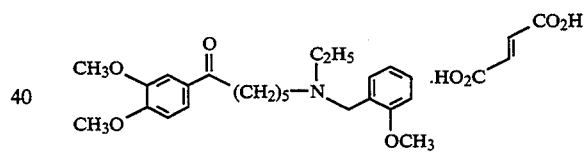

According to the same manner as Example 1, colorless crystals having melting point 111°–113° C. were obtained.

Elemental analysis C$_{24}$H$_{33}$NO$_4$.C$_4$H$_4$O$_4$ Calcd.: C 65.23 H 7.23 N 2.72 Found: C 65.04 H 7.11 N 2.64

EXAMPLE 3

N-[7-(3,4-dimethoxyphenyl)-7-oxo-6-phenylheptyl]-N-ethyl-N-[(2-methoxyphenyl)methyl]amine hydrochloride

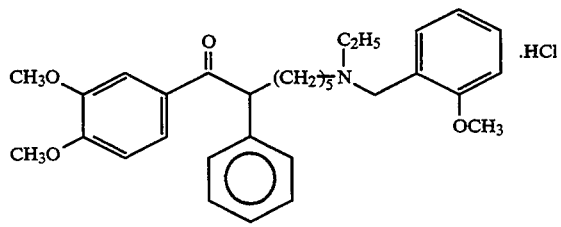

A solution of 7-bromo-1-(3,4-dimethoxyphenyl)-1-oxo-2-phenylheptane (0.8 g) prepared by Reference Example 2-2 and N-ethyl-N-[(2-methoxyphenyl)methyl]amine (0.65 g) in toluene (15 ml) was refluxed for 16 hours and then solvent was distilled off under reduced pressure. The remaining oily substance was subjected to column chromatograhy (eluent:ethyl acetate-methanol=20:1 (V/V)). The fractions containing the desired compound were pooled and then the solvent was distilled off under reduced pressure to give a colorless amorphous powder (0.74 g).

Elemental analysis $C_{31}H_{39}NO_4 \cdot HCl$ Calcd.: C 70.77 H 7.66 N 2.66 Found: C 70.59 H 7.61 N 2.48

EXAMPLE 4

According to the same manner as Example 1, the compounds shown in Table 2 were obtained.

dium hydroxide (10%), the product was extracted in dichloromethane and then dried over anhydrous sodium sulfate. The solvent was distilled off. The remaining oily substance and pyrrolidine (3 ml) were heated at 80° C. for 14 hours, and the reaction mixture was distributed between dichloromethane and an aqueous saturated solution of sodium bicarbonate, and the obtained organic layer was dried and the solvent was distilled off to give colorless needles (0.92 g).

The thus obtained crystals (0.92 g) and fumaric acid (0.28 g) were dissolved in methanol, and the solvent was distilled off. The residue was recrystallized from ethanol to give colorless crystals (1.1 g) having melting point 100°–102° C.

Elemental analysis $C_{25}H_{34}N_2O \cdot C_4H_4O_4$ Calcd.: C 70.42 H 7.74 N 5.66 Found: C 70.32 H 7.68 N 5.54

TABLE 2

$$\text{A} - \overset{O}{\underset{}{C}} - \underset{R^1}{\overset{}{CH}} - (CH_2)_n - \underset{}{\overset{C_2H_5}{N}} - CH_2R$$

| Compound No. | A | $R^1$ | n | R | Melting point (°C.) | Molecular formula | Elemental analysis calcd. (Found) | | |
|---|---|---|---|---|---|---|---|---|---|
| | | | | | | | C | H | N |
| 1 | 4-F-phenyl | H | 4 | phenyl | 113–116 | $C_{21}H_{26}FNO$ $\cdot C_4H_4O_4$* | 67.70 (67.61 | 6.82 6.69 | 3.16 3.09) |
| 2 | 4-pyrrolidino-phenyl | H | 4 | phenyl | 100–102 | $C_{25}H_{34}N_2O$ $\cdot C_4H_4O_4$* | 70.42 (70.40 | 7.74 7.69 | 5.66 5.62) |
| 3 | 4-pyrrolidino-phenyl | H | 4 | 2-OCH$_3$-phenyl | 139–140 | $C_{26}H_{36}N_2O_2$ $\cdot C_4H_4O_4$* | 68.68 (68.54 | 7.68 7.49 | 5.34 5.27) |

*fumarate

EXAMPLE 5

N-Ethyl-N-(phenylmethyl)-N-[6-(4-pyrrolidinophenyl)-6-oxohexyl]amine fumarate

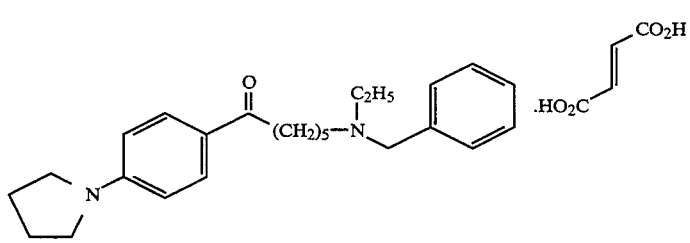

N-Ethyl-N-[6-(4-fluorophenyl)-6-oxohexyl]-N-phenylmethyl amine fumarate (1.5 g) prepared by Example 4-1 was dissolved in an aqueous solution of so-

EXAMPLE 6

N-Ethyl-N-[(2-methoxyphenyl)methyl]-N-[6-(4-pyrrolidinophenyl)-6-oxohexyl]amine fumarate

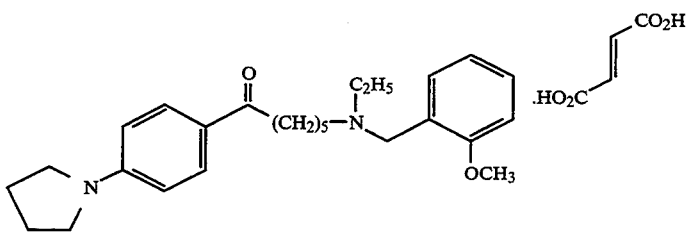

A solution of the compound prepared by Reference Example 2-3 (0.25 g) and N-Ethyl-N-[(2-methoxyphenyl)methyl]amine (0.24 g) in toluene (5 ml) was refluxed for 12 hours and then the solvent was distilled off under reduced pressure. The remaining oily substance was subjected to column chromatography (eluent:ethyl acetate—methanol=20:1 (V/V)) to give N-ethyl-N-[(2-methoxyphenyl)methyl]-N-[6-(4-fluorophenyl)-6-oxo-5-ethoxycarbonylhexyl]amine as an oily substance. The obtained oily substance and pyrrolidine (2 ml) were heated at 80° C. for 16 hours, and the product was dissolved in ethanol (3 ml) and after addition of a solution of potassium hydroxide (0.3 g) in water (0.6 ml), the mixture was refluxed for 6 hours. The solvent was distilled off under reduced pressure. To the residue was added water (10 ml), and the formed product was extracted in dichloromethane, then dried. The solvent was distilled off under reduced pressure. The remaining oily substance (0.17 g) and fumaric acid (48 mg) were dissolved in methanol, and the solvent was distilled off. The residue was recrystallized from ethanol to give colorless crystals (0.2 g) having melting point 139°–140° C.

Elemental analysis $C_{26}H_{36}N_2O_2 \cdot C_4H_4O_4$ Calcd.: C 68.68 H 7.68 N 5.34 Found: C 6 8.64 H 7.6 3 N 5.29

PREPARATION EXAMPLE 1

| | |
|---|---|
| (1) N-[7-(3,4-dimethoxyphenyl)-7-oxoheptyl]-N-ethyl-N-[(2-methoxyphenyl)methyl]amine hydrochloride (the compound obtained by Example 1) | 1 g |
| (2) Lactose | 197 g |
| (3) Corn starch | 50 g |
| (4) Magnesium stearate | 2 g |

(1), (2) and 20 g of corn starch were mixed, and the mixture was granulated with a paste prepared from corn starch (15 g) and water (25 ml). To the granulated product were 15 g of corn starch and (4), and the mixture was molded with a compression tablet molding machine to give 2,000 tablets each measuring 3 mm in diameter and containing 0.5 mg of (1).

PREPARATION EXAMPLE 2

| | |
|---|---|
| (1) N-[7-(3,4-dimethoxyphenyl)-7-oxyheptyl)-N-ethyl[(2-methoxyphenyl)methyl]amine hydrochloride (the compound obtained by Example 1) | 2 g |
| (2) Lactose | 196 g |
| (3) Corn starch | 50 g |
| (4) Magnesium stearate | 2 g |

(1), (2) and 20 g of corn starch were mixed, and the mixture was granulated with a paste prepared from corn starch (15 g) and water (25 ml). To the granulated product were added 15 g of corn starch and (4), and the mixture was molded with a compression tablet molding machine to give 2,000 tablets each measuring 5 mm in diameter and containing 1 mg of (1).

TEST EXAMPLE

The anticholinesterase activity of the compound of the invention was evaluated using (acetyl-[$^3$H])-acetylcholine. The $S_1$ fraction of a cerebral cortex homogenate from male Wistar rats was used as the cholinesterase source, (acetyl-[$^3$H])-acetylcholine as the substrate and the test compound of the invention as the test substance. The incubation was carried out for 30 minutes and after the reaction was terminated, the system was shaken with a toluene scintillator to thereby transfer [$^3$H]-acetic acid into the toluene layer. The radioactivity in the toluene layer was then measured with a liquid scintillation counter to estimate the anticholinesterase activity of the test compound.

The anticholinesterase activity of the test compound was expressed in 50% inhibitory concentration ($IC_{50}$). As a control, the anticholinesterase activity of physostigmine was also estimated in the same manner. The results are set forth in Table 3.

TABLE 3

| Compound (Example No.) | Anticholinesterase activity, $IC_{50}$ ($\mu M$) |
|---|---|
| 1 | 0.010 |
| 2 | 0.024 |
| 4-2 | 0.31 |
| 4-3 | 0.050 |
| Physostigmine | 0.22 |

It is apparent from the above results that the compounds of the present invention have excellent anticholinesterase activity.

What we claim is:

1. A method for promoting a brain function ameliorating action by inhibiting cholinesterase, which comprises administering to a mammal in need thereof an effective cholinesterase inhibiting amount of an aminoketone compound of the formula:

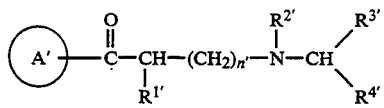

wherein ring A' represents a five through eight-membered cyclic group which may be substituted and which may contain one or two hetero atom(s) of O, S, N as ring-constituents; $R^{1'}$ represents a hydrogen atom or a hydrocarbon residue which may be substituted; $R^{2'}$ represents a hydrogen atom or a lower alkyl group; $R^{3'}$ represents an aromatic group which may be substituted; $R^{4'}$ represents a hydrogen atom, a lower alkyl group or an aromatic group which may be substituted; and n' represents an integer from 3 to 5, or a physiologically acceptable salt thereof.

2. The method according to claim 1, wherein the ring A' has one to three substituents selected from the group consisting of a $C_{1-4}$ alkoxy group, nitro, cyano, a halogen atom, a $C_{1-4}$ alkylcarbonylamino group, a $C_{1-4}$ alkylsulfonyl group, a 5- to 8-membered cycloamino group and a mono- or di-$C_{1-4}$ alkylamino group.

3. The method according to claim 1, wherein the ring A' in the formula means a benzene ring which may be substituted.

4. The method according to claim 3, wherein the benzene ring is substituted with a $C_{1-4}$ alkoxy group and/or a mono- or di-$C_{1-4}$ alkylamino group.

5. The method according to claim 1, wherein $R^{1'}$ is a hydrogen atom, a $C_{1-11}$ alkyl group, a $C_{2-4}$ alkenyl group, a $C_{2-4}$ alkynyl group, a $C_{3-7}$ monocyclic cycloalkyl group, a $C_{8-14}$ cross-linked cyclic saturated hydrocarbon or cyclic unsaturated hydrocarbon residue.

6. The method according to claim 1, wherein one of $R^{3'}$ and $R^{4'}$ is phenyl or naphthyl and the other is a hydrogen atom.

7. The method according to claim 1, wherein the compound is N-[7-(3,4-dimethoxyphenyl)-7-oxoheptyl]-N-ethyl-N-[(2-methoxyphenyl)methyl]amine hydrochloride.

8. The method according to claim 1, wherein the compound is N-[6-(3,4-dimethoxyphenyl)-6-oxohexyl]-N-ethyl-N-[(2-methoxyphenyl)methyl]amine fumarate.

9. The method according to claim 1, wherein the compound is N-[7-(3,4-dimethoxyphenyl)-7-oxo-6-phenylheptyl]-N-ethyl-N-[(2-methoxyphenyl)methyl]amine hydrochloride.

10. The method according to claim 1, wherein the compound is N-ethyl-N-[6-(4-fluorophenyl)-6-oxohexyl]-N-(phenylmethyl)amine fumarate.

11. The method according to claim 1, wherein the compound is N-ethyl-N-(phenylmethyl)-N-[6-(4-pyrrolidinophenyl)-6-oxohexyl]amine fumarate.

12. The method according to claim 1, wherein the compound is N-ethyl-N-[(2-methoxyphenyl)methyl]-N-[6-(4-pyrrolidinophenyl)-6-oxohexyl]amine fumarate.

13. The method of claim 1, wherein said compound is administered for the treatment of a disease selected from the group consisting of senile dementia, Alzheimer's disease, Huntington's chorea, hyperkinesia and mania.

14. The method of claim 1, wherein said compound is administered in a form selected from the group consisting of tablets, granules, capsules, injections and suppositories.

15. The method of claim 1, wherein said compound is administered orally.

16. The method of claim 15, wherein said effective amount is from about 0.001 to about 100 mg per day.

17. The method of claim 1, wherein said salt is a salt with an inorganic acid selected from the group consisting of hydrochloric acid, nitric acid, phosphoric acid, hydrobromic acid and sulfuric acid.

18. The method of claim 1, wherein said salt is a salt with an organic acid selected from the group consisting of acetic acid, formic acid, propionic acid, fumaric acid, maleic acid, succinic acid, tartaric acid, citric acid, malic acid, oxalic acid, benzoic acid, methanesulfonic acid and benzenesulfonic acid.

19. The method of claim 1, wherein said salt is a salt with an inorganic base selected from the group consisting of a sodium base, a potassium base, a calcium base, a magnesium base, and an ammonia base.

20. The method of claim 1, wherein said salt is a salt with triethylamine.

21. The method of claim 1, wherein said mammal is a human.

* * * * *